United States Patent [19]
Frankel et al.

[11] Patent Number: 5,811,244
[45] Date of Patent: Sep. 22, 1998

[54] **IN VITRO METHOD FOR IDENTIFYING A CLINICAL DISORDER ASSOCIATED WITH *NHE1* MUTATION**

[75] Inventors: Wayne N. Frankel; Gregory A. Cox; Cathleen M. Lutz, all of Bar Harbor, Me.; Jeffrey L. Noebels, Houston, Tex.

[73] Assignees: The Jackson Laboratory, Bar Harbor, Me.; Baylor College of Medicine, Houston, Tex.

[21] Appl. No.: 715,142

[22] Filed: Sep. 18, 1996

[51] Int. Cl.⁶ .................................................. G01N 33/53
[52] U.S. Cl. ................ 435/7.2; 435/4; 435/7.1; 435/375
[58] Field of Search ................ 435/4, 7.2, 7.21, 435/375

[56] References Cited

PUBLICATIONS

Sardet et al., Molecular cloning, primary structure, and expression of the human growth factor–activatable Na+/H+ antiporter. *Cell* 56: 271–280 (1989).

Morahan et al., Genetic and physiological association of diabetes susceptibility with raised Na+/H+ exchange activity. *Proc. Natl. Acad. Sci. USA* 91: 5898–5902 (1994).

Raley–Susman et al., Regulation of intracellular pH in cultured Hippocampal neurons by an Amiloride–insensitive Na+/H+ exchanger. *J. of Biol. Chem.* 256: 2733–2745 (1991).

Fliegel et al., Cloning and analysis of the human myocardial Na+/H+ exchanger. *Mol. Cell. Biochem.* 125 (2): 137–143 (1993).

Carim et al. (1995) Hepatology. vol. 21, pp. 1089–1098.

Schoenecker et al. (1994) vol. 29 pp. G892–G898 Gastroinen. Liver Physiol.

Chu et al. (1996) Neurology vol. 47, pp. 756–760.

*Primary Examiner*—John Ulm
*Assistant Examiner*—Prema Mertz
*Attorney, Agent, or Firm*—Kevin M. Farrell

[57] ABSTRACT

Disclosed is the identification of a mutation which is responsible for ataxia and epilepsy in a murine model system. More specifically, a mutation has been identified within the Nhe1 gene (also referred to as the Slc9a1 gene) which results in both ataxia and epilepsy. The specific mutation identified is an A to T transition at nucleotide 1639 which creates a premature stop codon. The identification of this mutation enables methods for the detection of clinical disorders associated with a defect in a cation exchanger (e.g., Nhe1).

6 Claims, No Drawings

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAGCAAGCAG GTTTCAGGC                                        19

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GACTGCTCTT CCGAAGGTCC                                       20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CTTGTTCCAA AGTCACATGC                                       20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CAGCGCAGCC ATTTATAGGC                                       20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CACGACAATG CCATCGATTC 20

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TATGGAGGGG TCAGAGGGC 19

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AGCAAGCGTC GAACCGCAGG 20

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TCTTGCGTTC TAGGATG 17

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TGGCTGCCCT TCTTTGTGGC 20

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGGACATCGA AGCCTGG 17

(2) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

GGATCAGTAT GATGCTTCGG    20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

TGTGGATCTC CTCGAAGACG    20

( 2 ) INFORMATION FOR SEQ ID NO:13:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

ACATTGGCCT GCTGGACACC    20

( 2 ) INFORMATION FOR SEQ ID NO:14:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

GAAGACGAAG AGCGGCTCG    19

( 2 ) INFORMATION FOR SEQ ID NO:15:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

GGACATCTTC CTCGGCTTCC    20

( 2 ) INFORMATION FOR SEQ ID NO:16:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:16:

CCAGTTCCAC TGGTGGGAGC                                                                                        20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

TCATCTTCCT CGGCGTCTCC                                                                                        20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

TCATGCCCTG CACAAAGACG                                                                                        20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TCCTCACCGC CATCATCACC                                                                                        20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CAATGGCCTG CTTCATCTCC                                                                                        20

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CCAGCTCATT GCCTTCTACC 20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GATCTTCTGC TCCAGCTGCC 20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

ACCAGATGCT GCTCCGGAGG 20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TCTGTGGGAC ACCCACTAGC 20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

CCTGACCTGG TTCATCAACA 20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CCTGACCTGG TTCATCAACT 20

IN VITRO METHOD FOR IDENTIFYING A CLINICAL DISORDER ASSOCIATED WITH *NHE1* MUTATION

BACKGROUND OF THE INVENTION

The epilepsies are a group of disorders characterized by chronic, recurrent, paroxysmal changes in neurologic function caused by abnormalities in the electrical activity of the brain. They are estimated to affect between 0.5 and 2 percent of the population and can occur at any age. Each episode of neurologic dysfunction is called a seizure. Seizures may be convulsive when they are accompanied by motor manifestations or may be manifest by other changes in neurologic function (i.e., sensory, cognitive, emotional events). Epilepsy can be acquired as a result of neurologic injury or a structural brain lesion and also can occur as a part of many systemic medical diseases. Epilepsy also occurs in an idiopathic form in an individual with neither a history of neurologic insult nor other apparent neurologic dysfunction and may have a genetic cause. Isolated, nonrecurrent seizures may occur in otherwise healthy individuals for a variety of reasons, and under these circumstances, the individual is not said to have epilepsy.

Treatment of a patient with a seizure disorder is directed at eliminating the cause of the seizures, suppressing the expression of the seizures, and dealing with the psychosocial consequences which may occur as a result of the neurologic dysfunction underlying the seizure disorder or from the presence of a chronic disability. Better understanding of the cellular basis for such disorders would result in more refined therapeutic approaches.

SUMMARY OF THE INVENTION

In one aspect, the present invention relates to a method for identifying a clinical disorder associated with a mutation in the Nhe 1 gene. DNA encoding Nhe1 is isolated from an individual to be tested. The nucleotide sequence of the isolated DNA which encodes Nhe1, or portions thereof, is then determined by conventional techniques. The determined nucleotide sequence of the isolated DNA which encodes Nhe1 is then compared to the nucleotide sequence of the gene encoding the wild-type. A difference between the compared nucleotide sequences is indicative of a clinical disorder associated with a mutation in the Nhe1 gene.

In another aspect, the invention relates to an oligonucleotide probe useful for diagnosing a clinical disorder in an individual, the clinical disorder being associated with a mutation in the Nhe1 gene. The oligonucleotide probes of the invention are characterized by the ability to hybridize specifically to a mutant allele of the Nhe1 gene.

In another aspect, the invention relates to a method for identifying a clinical disorder associated with a mutation in the Nhe1 gene by first providing isolated nucleic acid from an individual to be tested for the clinical disorder associated with a mutation in the Nhe1 gene. The isolated nucleic acid is then contacted with an oligonucleotide probe which hybridizes specifically to a mutant allele of Nhe1, but not specifically to a wild-type form of the Nhe1 gene, under stringent hybridization conditions. Following a wash step, specifically hybridizing probe is detected by conventional techniques.

The invention also relates to an expression-based method for identifying a clinical disorder associated with a mutation in the Nhe1 gene. DNA encoding Nhe1 is isolated from the individual and expressed using recombinant DNA techniques. The molecular weight of the expressed Nhe1 gene product is then determined and compared with the molecular weight of wild-type Nhe1 which is produced and assayed in an otherwise identical manner. A reduction in the molecular weight relative to that of wild-type is indicative of the clinical disorder associated with a mutation in the Nhe1 gene.

In another embodiment, the present invention relates to a method for identifying a clinical disorder associated with a defect in the function of a cation exchanger. This method involves assaying for the ability of the cells from an individual to regulate intracellular pH.

DETAILED DESCRIPTION OF THE INVENTION

The present invention is based on the discovery of a mutation which is responsible for ataxia and epilepsy in a murine model system. More specifically, a mutation has been identified within the Nhe1 gene (also referred to as the Slc9a1 gene) which results in both ataxia and epilepsy. As disclosed in the Exemplification section which follows, the specific mutation identified is an A to T transition at nucleotide 1639 which creates a premature stop codon.

Nhe1 is a ubiquitously expressed member of a family of genes that facilitates the pH dependent exchange of intracellular hydrogen ($H^+$) for extracellular sodium ($Na^+$). Nhe1 has been studied for its likely homeostatic role in pH and osmotic pressure regulation, but has not previously been suspected in neurological disorders such as epilepsy or ataxia. Based on the low levels of Nhe1 mRNA and the location of the nonsense mutation in the middle of the coding region, the defect is predicted to result in the elimination or substantial reduction in the levels of functional Nhe1 protein.

The cDNA sequence of the human Nhe1 gene has been previously reported (Fliegel et al., *Mol. Cell. Biochem.* 125: 137–143 (1993)). A comparison of the published human DNA sequence and the deduced amino acid sequence with the murine cDNA and deduced amino acid sequence reveals that a high degree of homology exists within the Nhe1 gene between these two species. In fact, this homology can exceed 97% over some long stretches. These stretches of homology include a 64 amino acid tract wherein human and mouse share 62 amino acids. This specific tract of amino acids includes near its center the lysine residue discussed above.

Thus, the present invention is based on the discovery that ataxia and epilepsy can be caused by a mutation in the Nhe1 gene. Ataxia is a general term which applies to a heterogenous family of disorders characterized by a disorder of balance and gait. As discussed above in the Background section, the epilepsies are a group of convulsion and seizure disorders characterized by chronic, recurrent, paroxysmal changes in neurologic function caused by abnormalities in the electrical activity of the brain. Grand mal epilepsy is characterized clinically by a generalized convulsion having a tonic and clonic phase. Petit mal (or absence) epilepsy is characterized clinically by momentary staring spells.

The treatment of individuals suffering from ataxia or epilepsy is directed at eliminating the cause of the disorder thereby suppressing the expression of the disorder. Thus, the fact that a subset of these disorders appears to be caused by pH imbalances which result from a mutation in the Nhe1 gene opens new avenues for therapy.

Thus, in one aspect the present invention relates to diagnostic screening techniques useful for the identification of mutations within the Nhe1 gene which are responsible for disorders such as ataxia and epilepsy. For example, in one embodiment the present invention relates to diagnostic methods wherein DNA encoding Nhe1 is isolated from an individual, and the sequence of the DNA is determined. This determined DNA sequence is then compared with the sequence of the wild-type gene (see Fliegel et al., *Mol. Cell. Biochem.* 125: 137–143 (1993)). Differences identified between the sequence of the DNA isolated from the individual, as compared with the wild-type sequence, are indicative of a clinical disorder associated with a mutation in the Nhe1 gene. Confirmation that the mutation is responsible for a functional defect can be obtained through functional assays described in greater detail below.

One convenient method for determining the sequence of the Nhe1 gene in an individual is through the production of cDNA. For example, mRNA can be isolated from the cells of an individual (e.g., white blood cells). cDNA is then produced from the mRNA, and the Nhe1 -specific cDNA is amplified by the polymerase chain reaction (PCR) using primers known to correspond to conserved regions. The amplified product is then sequenced using conventional techniques such as the dideoxy chain termination method. This determined sequence is then compared to the wild-type sequence (see Fliegel et al., *Mol. Cell. Biochem.* 125: 137–143 (1993)). A difference between the wild-type Nhe1 sequence and that of the determined cDNA sequence from the individual defines candidate deleterious mutations. To determine whether a candidate deleterious mutation is, in fact, responsible for the reduction or elimination of Nhe1 activity, a functional assay of the type discussed below can be applied.

One of skill in the art will recognize that a variety of reasonable alternatives to the approach described above are available. For example, rather than producing cDNA, genomic DNA can be amplified directly using the PCR technique. Such technical considerations represent experimental design alternatives.

In a second embodiment, the present invention relates to oligonucleotide probes useful for diagnosing clinical disorders of the type described above. Nucleic acid probes can be designed to enable the detection of a specific mutation which is identified within the Nhe1 gene. The probes hybridize specifically to a defined target sequence in a mutant Nhe1 gene, but not to the corresponding sequence in a wild-type Nhe1 gene, under stringent hybridization conditions. One of the possible sets of stringent hybridization conditions is 5 X SSPE (1 X SSPE is 0.15M NaCl, 1 mm Na-EDTA, 10 mm Na-phosphate, pH 7.0), 5 X Denhardt's solution (0.1% polyvinylpyrrolidone, 0.1% Ficoll, 0.1% BSA) at 45° C. Washing can then be carried out in 5 X SSPE at 45° C.

Following the identification of a mutation responsible for an Nhe1 defect (for example, using methods of the type described above), the design of oligonucleotide probes useful for the detection of the predetermined mutant sequence is a routine matter to one of skill in the art. Preferably, oligonucleotide probes range in size from about 10 nucleotides in length to about 30 nucleotides in length (longer probes can be used, but offer no substantial advantage over probes of the preferred size range). The nucleotide(s) of potential mismatch is centrally located in the design of the probe, and all other nucleotides in the oligonucleotide should be perfectly complementary with the target. The oligonucleotide probes can be designed to hybridize to either the sense strand, or the antisense strand, when using cDNA or DNA as a target.

The probes can be used for diagnosis of the disorder in presymptomatic individuals, for prenatal diagnosis, or refinement of a prior diagnosis. Such diagnostic methods are performed by isolating nucleic acid from an individual and testing the diagnostic probes of the invention for the ability to hybridize to the isolated nucleic acid. For those mutations which fall within an exon sequence, the isolated nucleic acid can be genomic DNA, cDNA or mRNA which corresponds to the disclosed target. The isolated nucleic acid can be amplified, for example by the polymerase chain reaction, prior to hybridization diagnosis. As discussed above, the diagnostic hybridization is carried out under stringent hybridization conditions so that the diagnostic probes do not hybridize specifically to the corresponding wild-type sequence. In a preferred embodiment, the isolated nucleic acid is fixed to a solid support (e.g., nitrocellulose filter) using standard techniques.

In another embodiment, mutation in the Nhe1 gene can be detected by the expression of cDNA encoding Nhe1, followed by analysis of the encoded product. For example, cDNA (produced as described above) can be inserted into an expression vector and the vector can be used to transform cells. Such vectors contain all necessary regulatory signals to promote the expression of a DNA sequence of interest. Expression vectors are typically either prokaryote specific, or eukaryote specific. However, vectors have been developed which can promote the expression of a DNA sequence of interest in either a prokaryotic or eukaryotic system. Such vectors are known as shuttle vectors.

Prokaryotic expression vectors are useful for the preparation of large quantities (e.g., up to milligram quantities) of the protein encoded by the DNA sequence of interest. Eukaryotic expression vectors are useful when the addition of carbohydrate side chains, (i.e. glycosylation) to the protein is important. The carbohydrate sidechains can affect the properties of a protein in a variety of ways including, for example, the ability of the protein to function in vivo or in vitro; the ability of the protein to form a complex and associate with other proteins or nucleic acids; and ability of the protein to bind to an antibody or other molecule specific for the protein of interest.

Protein can also be expressed in cell free systems which include the reticulocyte lysate system. These expression systems have several advantages over the production of protein in a prokaryotic or eukaryotic cell. These include the ease of use, the cost per reaction and the amplification of desired product with minimal contaminating protein. The primary disadvantage of a cell free system is a reduction in the amount of protein produced due to the limited quantity of starting material (e.g., amino acids) added at the beginning of the reaction.

Expressed protein can be examined by means routine to one of skill in the art. Preferably, expressed protein can be separated and its size deduced by electrophoresis using a polyacrylamide gel (PAGE). PAGE is sensitive enough to allow small differences in the size of two proteins to be identified. This is especially useful when attempting to identify isoforms or truncated versions of a particular protein, such as the mutated form of Nhe1 disclosed in the Exemplification. To visualize protein bands within a PAGE gel, it is a common technique to stain the gel with either coomassie blue or silver stain.

In another embodiment, the present invention relates to the diagnosis of ataxia or epilepsy by determining the ability of the cells from an individual to regulate intracellular pH levels. As discussed above, Nhe1 has been studied for its homeostatic role in pH and osmotic pressure regulation, but has not previously been suspected in neurological disorders such as epilepsy or ataxia. In light of this role, cells containing a defective copy of the Nhe1 gene are predicted to exhibit an inability to regulate intracellular pH.

A variety of assays for determining the ability of a cell to regulate intracellular pH can be designed. For example, Morahan et al. (*Proc. Natl. Acad. Sci. USA* 91: 5898–5902 (1994)) discloses a method for determining intracellular pH. Raley-Susman et al. (*J. Biol. Chem.* 266: 2733–2745 (1991)) discloses an acid-loading assay for determining the ability of a cell to regulate intracellar pH. The Nhe1 gene product is known to be specifically inhibited by the drug amiloride. By conducting assays of the type described by Raley-Susman et al., in the presence or absence of amiloride, one can determine whether the cells under study contain a functional copy of the Nhe1 gene.

In another embodiment, the present invention relates to therapeutic applications. More specifically, individuals identified with a functional defect in Nhe1 (or another gene which results in the inability to regulate pH) can be treated with drugs selected from a group of drugs which are known to interact with cation exchangers. One such drug which can be used to ameliorate the effects of the Nhe1 mutation is arginine vasopressin (AVP). This drug is known to have the ability to stimulate an alternative cation exchanger. Treatment of cells containing a defective copy of the Nhe1 cation exchanger with a drug known to stimulate the activity of an alternative cation exchanger would be predicted to ameliorate both the effects of the Nhe1 mutation and the effects of the genetic disorder. As mentioned previously, epilepsy-related therapies are most often treated symptomatically at the present time.

The therapeutic methods described above are indicated in the event that the assays designed to determine the ability of a cell of an individual to regulate intracellular pH reveal decreased Nhe1 activity (as was seen in the murine model system disclosed in the Exemplification). It is possible, however, that the cells of an individual may exhibit enhanced Nhe1 activity. This could occur, for example, if the Nhe1 gene were overexpressed in the cells of an individual. Overexpression, like underexpression or expression of a defective product, can result in an intracellular pH imbalance.

To ameliorate the effects of enhanced Nhe1 activity, the diuretic amiloride and its analogue ethylisopropyl amiloride (EIPA) are indicated. These drugs are potent inhibitors of $Na^+/H^+$ cation exchangers in vivo. They function by directly binding to and inhibiting the Nhe1 molecule, most likely at the $Na^+$ binding site. Alternatively, drugs which stimulate anion exchange activity can be used. Examples include 4'-acetamido-4'-isothiocyanostilbene-2,2'disulfonic acid (SITS), 4,4'-isothiocyanostilbene2,2'-disulfonic acid (DIDS) or similar reagents.

EXEMPLIFICATION

Inherited excitability defects in mice give rise to paroxysmal abnormal oscillations in thalamocortical circuits that model essential elements of human generalized absence epilepsy. Single locus mutations show cortical spike-wave rhythms discharging at frequencies of 6/sec or higher, but their homology with human inherited 3/sec epilepsy syndromes remains uncertain. Disclosed herein is the phenotypic description, genetic mapping and identification of the gene which underlies a spontaneous mouse mutant with ataxia and a novel epilepsy phenotype. The recessive slow-wave epilepsy (swe) mutation arose spontaneously on the SJL/J inbred strain and maps to the distal portion of Chromosome 4. EEG recordings reveal frequent (~120/hour) episodes of generalized, bilaterally symmetric wave, and wave-spike activity. The rhythmic periodicity ranges from 3–4.5/sec. The spike-wave patterns are associated with behavioral immobility, are suppressed by ethosuximide, and disappear with age, similar to human "petit mal" epilepsy. The 3/sec spike-wave discharges in swe mutants are the first to accurately resemble those in childhood generalized epilepsy. Occasional spontaneous generalized tonic-clonic seizure episodes, which usually result in death, have also been observed in swe homozygotes as early as 14–18 days postnatal, and the 50% mortality rate of affected mice on the SJL background is presumed to be the result of these convulsions.

In order to identify the gene responsible for the phenotype described above, a high resolution genetic map was constructed using (SJL/J-swe x C57BL/6J) F1 and (SJL/J-swe x B6.SPRET-distal Chr 4) F1 intercross mice. All candidate genes known to map to the region except the sodium/hydrogen exchanger (Nhe1, aka Slc9a1) had been excluded by analysis of F2 recombinants (zero recombinants in 1526 meioses). RT-PCR and northern analysis revealed a greater than 90% reduction of Nhe1 mRNA levels in brain and prompted SSCP mutation screening of the Nhe1 coding region. An SSCP difference was detected between swe/swe homozygotes and the SJL/J parental strain in the middle of the coding region of the gene. Subsequent sequencing of the RT-PCR product revealed a single A to T transition at nucleotide 1639 that creates a premature stop codon which would truncate the protein after 441 amino acids and delete the final 379 C-terminal amino acids. Based on the low levels of Nhe1 mRNA and the location of the nonsense mutation in the middle of the coding region, the defect is predicted to result in the lack of expression of a functional Nhe1 protein. Nhe1 is a ubiquitously expressed member of a family of genes that facilitates the pH-dependent transport of hydrogen ($H^+$) ions out of cells in exchange for extracellular sodium ($Na^+$). Nhe1 has been studied for its likely homeostatic role in pH and osmotic pressure regulation, but has not previously been suspected for a role in neurological disorders such as epilepsy or ataxia. The swe mutant demonstrates that specific thalamocortical oscillation frequencies are linked to the function of a specific sodium/hydrogen exchange protein, and provides a critical new entry point into the molecular dissection of mechanisms regulating 3/sec spike-wave epileptogenesis.

METHODS

Chromosomal Mapping

Genomic DNA was prepared from tail tips using a salt-out procedure as previously described (Taylor et al., *Genomics* 16: 380–394 (1994)). REVEAL-PCR was done as previously described (Frankel et al., *Mamm. Genome* 5: 659–662 (1994); Frankel et al., *Mamm. Genome* 6: 830–838 (1995); and, Kaushik and Stoye, *Mamm. Genome* 5: 688–695 (1994)). Results showing linkage were obtained using an oligonucleotide primer from the ETn LTR (JS167: 5'-GAGCAAGCAGGTTTCAGGC-3' SEQ ID NO:1) and one from a B2 repeat (JS135: 5'-GACTGCTCTTCCGAA GGTCC-3' SEQ ID NO:2). Initial estimates of linkage were done by contingency Chi-square analysis assuming a recessive mode of inheritance for swe in intercross progeny. For SSLP mapping, three mice of questionable affection status were eliminated from the analysis, and two unaffected mice were added. SSLP markers were typed on these DNAs as previously described (Frankel et al., *Mamm. Genome* 5:

659–662 (1994)). Gene order was determined by minimizing double-crossovers, while two-point LOD scores and multipoint map distances were determined using the computer program MAPMAKER (Lander et al., *Genomics* 1: 174–181 (1987)). All analyses were aided by use of the Macintosh-friendly computer program Map Manager (Manly and Elliot, *Mamm. Genome* 1: 123–127 (1991)). Map positions of candidate genes were inferred from the Mouse Genome Database (http://www.informatics.jax.org/mgd.html). For construction of a high resolution genetic map of the swe locus, 602 (SJL/J-swe x C57BL/6J) F1 intercross and 161 (SJL/J-swe x B6.SPRET-distal Chr 4) F1 intercross mice were phenotyped and genotyped to identify recombinants using the SSLP markers D4Mit309, D4Mit71, D4Mit204, and D4Mit339.

Candidate Gene Mapping

The Nhe1 gene was mapped relative to F2 recombinants using an SSLP identified between SJL/J and C57BL/6J in the promoter of the gene using primers corresponding to nucleotides 843-1071 of the Nhe1 promoter (Genbank accession# L3752 5). The primers used were: mNhe1 F5'-CTTGTTCCAAAGTCACATGC-3' SEQ ID NO:3 and R 5'-CAGCGCAGCCATTTATAGGC-3' SEQ ID NO:4. Neural Syndecan 3 (Synd3) was mapped by SSCP using the primers SyndF 5'-CACGACAATGCCATCGATTC-3' SEQ ID NO:5 and SyndR 5'-TATGGAGGGGTCAGAGGGC-3' SEQ ID NO:6 which amplify a 202 bp fragment of the gene.

The serotonin receptor gene 1D (5Htr1d) was mapped by SSCP using the primers 3F 5'-AGCAAGCGTCGAACCG CAGG-3' SEQ ID NO:7 and 3R 5'-TCCTCTTGCGTTCT AGGATG-3' SEQ ID NO:8 which amplify a 432 bp fragment of the gene (Genbank accession# L20335).

The serotonin receptor gene 6 (5Htr6) was mapped by SSCP using the primers F 5'-TGGCTGCCCTTCTTTGTG GC-3' SEQ ID NO:9 and R 5'-AGGACATCGAAGCCTGG-3' SEQ ID NO:10 which amplify an approximately 265 bp fragment of the gene (Genbank accession# L41146).

Northern Blot Analysis

Total RNA was prepared from the brains of swe/swe mutants and +/+ control littermates, separated on a 1.2% Agarose/formaldehyde gel and transferred to hybond N+ nylon membrane (Amersham). The membrane was probed with the $\alpha$-p$^{32}$ labeled (Prime-It, Stratagene) 771 bp RT-PCR product from the 5' end of the Nhe1 cDNA (mNhe1 F1 5'-GGATCAGTATGATGCTTCGG-3' SEQ ID NO:11 and R1 5'-TGTGGATCTCCTCGAAGACG-3' SEQ ID NO:12) corresponding to nucleotides 308-1078 of the mouse Nhe1 mRNA sequence (Genbank accession# U51112).

SSCP Mutation Screening and Sequencing

One microgram of total brain RNA from swe/swe mutants and +/+ control littermates was reverse transcribed with random hexamers and oligo-dT as previously described (Cox et al., *Nature Genetics* 4: 87–93 (1993)). For SSCP analysis, the Nhe1 cDNA was amplified by RT-PCR (94° C. x1 min, 60° C.x1 min, 72° C.x1 min for 35 cycles) using seven overlapping oligonucleotide primer pairs covering the 2463 bp coding region. Primer pairs: mNhe1 F1 and R1 (as described above); (F2 5'-ACATTGGCCTGCTGGACACC -3' SEQ ID NO:13 and R2 5'-GAAGACGAAGAGCGGC TCG-3' SEQ ID NO:14) nucleotides 989-1332; (F3 5'-GGACATCTTCCTCGGCTTCC -3' SEQ ID NO:15 and R3 5'-CCAGTTCCACTGGTGGGAGC-3' SEQ ID NO:16) nucleotides 1194-1560; (F4 5'-TCATCTTCCTCGGCGTC TCC -3' SEQ ID NO:17 and R4 5'-TCATGCCCTGCACA AAGACG-3' SEQ ID NO:18) nucleotides 1511-1819; (F5 5'-TCCTCACCGCCATCATCACC -3' SEQ ID NO:19 and R5 5'-CAATGGCCTGCTTCATCTCC-3' SEQ ID NO:20) nucleotides 1766-2086; (F6 5'-CCAGCTCATTGCCTTCT ACC -3' SEQ ID NO:21 and R6 5'-GATCTTCTGCTCCA GCTGCC-3' SEQ ID NO:22) nucleotides 2040-2367; (F7 5'-ACCAGATGCTGCTCCGGAGG -3' SEQ ID NO:23 and R7 5'-TCTGTGGGACACCCACTAGC-3' SEQ ID NO:24) nucleotides 2318-2804. RT-PCR products were sequenced with the primers used to amplify the fragments by incorporation of $\alpha$-p$^{32}$ dCTP (NEN) using the Perkin-Elmer Ampli-Taq Cycle-Sequencing Kit. Allele-specific PCR primers were designed to amplify the wild-type or mutant sequence when paired with the oligonucleotide primer R4 to confirm the sequence of the mutation and to facilitate genotyping. The wild-type PCR primer (F4.1A 5'-CCTGACCTGGTT CATCAACA-3' SEQ ID NO:25) and the swe mutant primer (F4.1T 5'-CCTGACCTGGTTCATCAACT-3' SEQ ID NO:26) differ only in the identity of the 3' nucleotide.

Histology

Young (22–28 days of age postnatal) and adult (41–47 or 117–123 days) affected or unaffected mice from the SJL stock or B6SJLF2 progeny were perfused in Bouin's fixative, brain sections were cut, mounted and stained with H&E AND LFB-CV for light microscopic analysis.

RESULTS

Neurological Phenotype of swe/swe Mutants
Ataxia

Affected swe mice are initially recognizable on the basis of their ataxic gait, first readily evident between 11–14 days postnatal. Mutants show a moderate to severe degree of locomotor ataxia, most prominent in the hindlimbs, producing coarse truncal instability during movement. Affected mice show no headtossing or circling, and they have little difficulty orienting themselves in a swim test. There is no limb weakness, and affected mice appear to have no behavioral abnormalities other than ataxia and seizures. Heterozygous swe mice appear normal.

Mortality and Tonic-clonic Seizures

In the founder inbred SJL stock, about half of the presumed swe/swe animals survive to weaning. Of the surviving swe/swe mice, most are found dead or moribund by 40 days, although an occasional affected mouse will survive for several months. Many of the swe/swe mice that die are found with extended hind limbs, and clenched forepaws. On both the SJL and the (C57BL/6J x SJL)F2 backgrounds, rare spontaneous generalized and tonic-clonic seizure episodes have been observed in affected or known swe/swe individuals as early as 14 days postnatal, but not in unaffected, or known heterozygotes. Seizures begin with several seconds of wild running, followed by a brief tonic-clonic convulsive behavioral seizure pattern. The convulsions typically last less than one minute. In at least two instances where tonic-clonic seizures were observed visibly, they resulted in immediate death.
Spike-wave Seizures Chronic EEG recordings from young swe/swe mice reveal frequent episodes of generalized, bilaterally symmetric wave, and wave-spike activity with a rhythmic periodicity ranging from 3–4.5/sec. The cortical seizures are always preceded by waves, which may appear maximal at the outset or grow in amplitude during the discharge; in some longer discharges, the spike component is diminished, and is either absent or buried in the wave. Both the wave patterns and the wave-spike bursts are specifically associated with complete behavioral arrest throughout the duration of the synchronous discharge. Each seizure is followed by loss of the wave and immediate resumption of the preictal EEG pattern and behavior. The interictal EEG of the homozygote consists of predominant low voltage, high frequency activity identical to that seen in +/swe and +/+ control mice. No 6–7/sec or more frequent spike-wave discharges were ever present in swe/swe mutants. Both the shorter wave-spike bursts and longer wave patterns associated with behavioral arrest are rapidly abolished by intraperitoneal injection of ethosuximide (50–100 mg/kg).

Genetic Background and Seizure Expression

There is a significant influence of genetic background on the developmental onset and severity of the swe epilepsy phenotype. Homozygous swe/swe on the founder SJL background show no cortical spike-wave phenotype when recorded. Within 2–3 weeks, spike-wave discharges were recorded, but discharges are predominantly brief (<1.5 sec) and rare (1–4/hour). Of all SJL swe/swe mutants at two months of age, none progressed in either spike-wave seizure frequency or duration, and in mice surviving until 9–10 months of age, no seizure discharges are present.

In contrast, the amount of spike-wave seizure activity is strikingly enhanced in mutants derived from the SJL x C57BL/6J intercross. In each homozygote, very frequent 3/sec seizure activity (~120/hour) are present by 4 weeks of age, and remain maximal for several months. Seizures in these mice are also longer in duration, and individual episodes range from 1–68 secs. By 9–10 months of age, swe/swe mutants on this background show no evidence of spike-wave activity. Heterozygotes on both genetic backgrounds show no evidence of: spike-wave abnormalities in prolonged EEG recordings, tonic-clonic convulsions, or a shorter lifespan than wild type mice.

Neuropathology

Serial brain sections reveal ongoing neuronal degeneration in cerebellar deep nuclei at a developmental stage compatible with the onset of ataxia in the mutant. On both genetic backgrounds, young (3 wk) mutants show enlarged pale neurons with swollen lucent nuclei throughout the deep cerebellar nuclear regions, with excessive surrounding glia cells. Scattered dystrophic axons are seen in and around the cerebellar molecular layer in some affected mice, but there is no apparent thinning of the granule cell layer, apparent loss of Purkinje Cells, or abnormal patterns of cerebellar cortical foliation. No other cytopathology is visible throughout the remainder of the mutant brain. Sections in a 5 month old mutant show that the degenerating deep cerebellar neurons seen in younger mice have disappeared by this age, and there is no evidence of late onset cytopathologic change in other brain regions.

Genetic Mapping of the swe Locus

The recessive swe mutation arose spontaneously on the SJL/J inbred strain, and its chromosomal location was determined in (C57BL/6J x SJL/J-swe) F2 progeny using the method of REVEAL-PCR which exploits endogenous provirus and short interspersed repeat sequence (SINE) variation amongst mouse strains. Multiple REVEAL-PCR products from various genomic regions failed to show linkage with swe in 22 apparently affected intercross progeny. However, a primer of ETn origin (JS167) paired with a B2 repeat sequence primer (JS135), revealed a C57BL/6J-derived band that was absent (i.e. swe/swe like) from eleven of 22 progeny (expect 5.5 for non-linkage), and an SJL-derived band absent (i.e. +/+ like) from two of 22 progeny (expect 5.5 for non-linkage). These two bands did not recombine from each other and mapped to distal Chr 4 in BXD RI strains (21/22 strains concordant with the marker Tel4q). Assuming the two bands were alleles of the same locus, and including data from unaffected progeny, linkage was suggested ($X^2$=8.9, p<0.01). Simple sequence length polymorphisms (SSLP) that span mid-distal Chr 4 were typed in 19 unambiguously affected and 22 unaffected intercross progeny. Strong evidence for linkage was observed with D4Nds2 (LOD 9.6), D4Mit13 (LOD 15.6) and D4Mit42 (LOD 13.8). Multipoint analysis suggested the map distances and gene order D4Mit9-(15 cM)-D4Nds2-(10 cM)-swe-(2 cM)-D4Mit13-(7 cM)-D4Mit42.

In order to identify the swe gene, a high resolution genetic map of the swe locus (1526 fully informative meioses) was constructed by analyzing the genotype and phenotype of 602 (SJL/J-swe x C57BL/6J) F2 progeny and 161 (SJL/J-swe x B6.SPRET-distal Chr 4) F2 progeny with the SSLP markers D4Mit309 (0.98 cM proximal), D4Mit71 and D4Mit204 (nonrecombinant), and D4Mit339 (0.07 cM distal). The resolution of the map allowed several candidate genes known to map to the region, including the serotonin receptors 1d and 6 (5htr1d and 5htr6) and neural syndecan 3 (Synd3) to be excluded by analysis of F2 recombinants. However, the sodium/hydrogen exchanger (Nhe1, aka Slc9a1) could not be excluded as a candidate for the swe mutation (zero recombinants in 1526 meioses).

Mutation Detection

RT-PCR and northern analysis revealed a greater than 90% reduction of Nhe1 mRNA levels in brain and prompted SSCP mutation screening of the Nhe1 coding region. An SSCP difference was detected between swe/swe homozygotes and the SJL/J parental strain in the middle of the coding region of the gene (nucleotides 1511-1819). Subsequent sequencing of the RT-PCR product revealed a single A to T transition at nucleotide 1639 that creates a premature stop codon which would lead to truncation of the protein after 441 amino acids and delete the final 379 C-terminal amino acids. The mutation results in the change of an AAG (Lys) codon into a TAG (stop) between the putative transmembrane domains nine and ten. In order to confirm the sequence of the mutation and facilitate precise genotyping, allele-specific PCR primers were generated which used the mutant or wild-type nucleotide as the most 3' base in the primer. The allele-specific PCR confirmed the sequence of the mutation and allows for rapid determination of carrier status in unaffected F2 progeny. Based on the low levels of Nhe1 mRNA and the location of the nonsense mutation in the middle of the coding region, the swe defect is predicted to result in the lack of expression of a functional Nhe1 protein.

We claim:

1. An in vitro method for identifying a clinical disorder in an individual associated with a defect in the function of the Nhe1 gene product, the method comprising:
   a) providing a cell type from the individual in which said cell type expresses the Nhe1 gene product;
   b) incubating the cell type of step a) in the presence or absence of a specific inhibitor of the Nhe1 gene product; and
   c) determining the ability of the cell type of step b) to regulate pH in the presence or absence of the specific inhibitor of the Nhe1 gene product, the identification of a cell type which is unable to regulate pH in either the presence or the absence of the specific inhibitor of the Nhe1 gene product being indicative of a clinical disorder associated with a defect in the function of the Nhe1 gene product.

2. A method of claim 1, wherein the clinical disorder is epilepsy.

3. A method of claim 2, wherein the clinical disorder is petit-mal epilepsy.

4. A method of claim 2, wherein the clinical disorder is grand-mal epilepsy.

5. A method of claim 1, wherein the clinical disorder is ataxia associated with intention tremor and wobbliness.

6. The method of claim 1 wherein the specific inhibitor of the Nhe1 gene product is amiloride.

* * * * *